United States Patent [19]

Badoz et al.

[11] Patent Number: 5,797,747
[45] Date of Patent: Aug. 25, 1998

[54] METHOD FOR USING ENDODONTIC INSTRUMENT FITTED ON A VIBRATING HAND-PIECE

[75] Inventors: Jean-Marie Badoz, Pontarlier; Paul Calas, Toulouse; Jean-Marie Vulcain, Vitre, all of France

[73] Assignee: Micro Mega International Manufactures, S.A., Besancon, France

[21] Appl. No.: 561,448

[22] Filed: Nov. 21, 1995

[30] Foreign Application Priority Data

Nov. 21, 1994 [FR] France ................. 94 14058

[51] Int. Cl.$^6$ ..................................... A61C 5/02
[52] U.S. Cl. ........................... 433/224; 433/102
[58] Field of Search ..................... 433/102, 118, 433/119, 124, 125, 165, 224

[56] References Cited

U.S. PATENT DOCUMENTS

| | | | |
|---|---|---|---|
| 1,818,627 | 8/1931 | Kerr | 433/224 |
| 4,299,571 | 11/1981 | McSpadden | 433/102 |
| 4,392,827 | 7/1983 | Martin | 433/224 |
| 4,889,487 | 12/1989 | Lovaas | 433/102 |
| 4,992,048 | 2/1991 | Goof | 433/102 |
| 5,094,617 | 3/1992 | Carr | 433/224 |
| 5,104,316 | 4/1992 | McSpadden | 433/102 |
| 5,110,291 | 5/1992 | Randin | 433/102 |
| 5,197,880 | 3/1993 | Lovaas | 433/102 |
| 5,320,530 | 6/1994 | Fong | |
| 5,642,998 | 7/1997 | Riitano | 433/224 |

FOREIGN PATENT DOCUMENTS

| | | | |
|---|---|---|---|
| 2575950 | 7/1986 | France | |
| 672313 | 2/1939 | Germany | 433/102 |

OTHER PUBLICATIONS

"The Endodontic File is a Disposable Instrument", by Reza B Kazemi, DMD, et al., Journal of Endodontics, vol. 21, No. 9, Sep. 1995, pp. 451–455.

"Hardness and Strength of Endodontic Files and Reamers", Peter John Brockhurst, and Ian Denholm, Journal of Endodontics, vol. 22, No. 2, Feb. 1996, pp. 68–70.

"Revision to American National Standards/American Dental Association Specification No. 28* For Root Canal Files and Reamers, Type K", *Approved Jun. 30, 1988, Effective Jun. 1989, ANSI/ADA Specification No. 28—1988, pp. 1–17.

*Primary Examiner*—Ralph A. Lewis
*Attorney, Agent, or Firm*—Weiser and Associates, P.C.

[57] ABSTRACT

The invention relates to an endodontic instrument which can be fitted on a vibratory handpiece (1) for the treatment of a tooth canal or the retreatment thereof, wherein it is made up of a rigid proximal portion constituting the sleeve which allows it to be fixed to the vibratory handpiece (1), of a median portion (4) which is also rigid and whose axis forms an angle (x) with the proximal portion, and of a distal portion (5) whose axis at the end forms an angle (y) with the median portion in the direction opposite that of the proximal portion, said distal portion being of a general conical line and of a dimension at the tip permitting its penetration into the canal.

8 Claims, 1 Drawing Sheet

METHOD FOR USING ENDODONTIC INSTRUMENT FITTED ON A VIBRATING HAND-PIECE

BACKGROUND OF THE INVENTION

1. Field of the Invention

The present invention relates to the field of endodontic instruments. It relates more particularly to an instrument or family of instruments permitting widening of the tooth canal for the purpose of its treatment and filling.

2. Description of the Related Art

There are at present a large number of endodontic instruments which, together with the associated methods, allow canal preparation to be carried out, either manually or mechanically, that is to say with the aid of a handpiece supporting the endodontic instrument.

However, during the treatment following opening of the pulp chamber, the practitioner very often encounters difficulties in locating the canal entrance, particularly in the case of multirooted teeth. Indeed, the end of the canal instruments intended to engage deep within the canal is often too flexible to permit the canal entrance to be cleared. The solution currently used is to "scrape" the bottom of the pulp chamber with a manual curette, which is not easy, all the more so since in this case one succeeds in revealing the canal entrance without creating a widening which will permit easy penetration of the instrument or instruments intended for the preparation of the radicular portion of the canal.

SUMMARY OF THE INVENTION

The primary object of the present invention is to provide an instrument which, when used on a handpiece conferring vibration upon it, makes it possible, on the one hand, to clear the canal entrance and, on the other hand, to widen the latter over a short distance which does not go beyond the upper third of the root.

Another object of the invention is to achieve an enlargement of the canal entrance in such a way as to afford easy penetration of the instruments which will follow.

A further object of the invention is to produce an instrument by means of which it is possible to achieve the above objects while at the same time avoiding any risk of perforation of the pulp floor or of the canal walls.

All these objects are achieved by virtue of an endodontic instrument which can be fitted on a vibratory handpiece for the treatment of a tooth canal or the retreatment thereof, wherein it is made up of a rigid proximal portion constituting the sleeve which allows it to be fixed to the vibratory handpiece, of a median portion which is also rigid and whose axis forms an angle (x) with the proximal portion, and of a distal portion whose axis at the end forms an angle (y) with the median portion in the direction opposite that of the proximal portion, said distal portion being of a general conical line and of a dimension at the tip permitting its penetration into the canal.

In a preferred manner, the instrument according to the invention has the distinguishing feature that the cutting geometry of its distal end is chosen from among (K file profile, H file profile, barbs, polygonal profiles).

Also in a preferred manner, the end of the distal portion is rounded.

Finally, in order to permit the resumption of dental treatment, the distal portion is long and fine and is bent at approximately 90° in relation to the median portion.

BRIEF DESCRIPTION OF THE DRAWINGS

The present invention will be better understood with the aid of the description which follows, with reference being made to the following attached figures.

DESCRIPTION OF THE PREFERRED EMBODIMENTS

Figure 1:
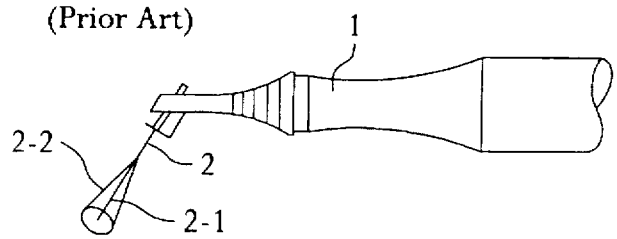
FIG. 1 represents a view of a vibratory handpiece of the prior art, provided with a vibrational instrument.

FIG. 1 shows a handpiece (1) provided with a canal instrument (2) of known type, for example the one described in the French Patent 2 575 950. In the rest position, the instrument is located in the position 2-1. When excited, it moves out of this position and about the envelope 2—2. This type of movement is obtained by virtue of the flexibility of the instrument.

Figure 2:
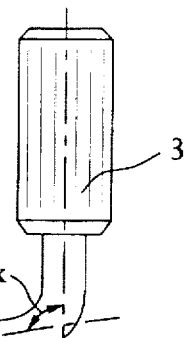
FIG. 2 represents a view of an instrument according to the present invention.
Figure 3:
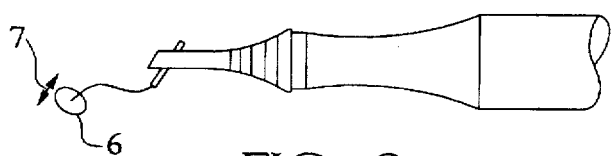
FIG. 3 represents an instrument according to the invention mounted on a handpiece, describing the vibrational movement of the tip.
Figure 4:
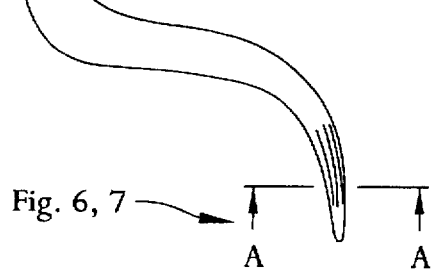
FIG. 4 represents a non-limiting embodiment of the invention.

FIG. 2 shows a non-limiting embodiment of the instrument according to the present invention, which instrument is made up of a rigid proximal portion or sleeve (3), preferably provided with striations which permit its retention in the head of a handpiece (1), and the diameter of which will be formed as a function of the stresses of fixing on the handpiece, a median portion (4) forming an angle (x) with the axis of the sleeve, and a distal portion (5) whose axis at the end forms an angle (y) with the median portion in the direction opposite that of the proximal portion. Since all these portions are rigid, the vibrations originating from the handpiece are translated into the movements represented in FIG. 3, that is to say without or almost without elastic deformation of the instrument. That is to say that the tip of the instrument is displaced along a curve (6), which is here represented as oval, but which is in fact dependent on the handpiece or rather on its mode of excitation, in combination with a to and fro movement (7).

It is easy to appreciate the advantage of the geometry of this instrument which, whatever the mode of excitation of the sleeve into vibration by the handpiece (1) (general multidirectional excitation), creates, at the tip of the instrument, a vibration similar to that given to a straight instrument, to which is added a longitudinal vibration of the distal portion. In this way, with the instrument being excited into vibration, it suffices for the practitioner to displace it on the pulp floor so that, on the one hand, he removes the material filling the canal entrance by "digging", and when he is in line with the entrance, he introduces the instrument therein, guaranteeing its positioning.

Figure 6:
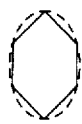
FIGS. 6 and 7 are non-limiting examples of profiles, according to the invention, formed at the cutting level AA in FIG. 4.
Figure 7:

In order to permit widening of the canal over a short length, it will be possible to provide the instrument with cutting shapes at its distal portion, which shapes can be either known profiles of the K or H file type, or barbs, or else polygonal profiles without helix, such as those in FIGS. 6 and 7 for example.

Since the distal portion is provided with a cutting geometry, it will be possible, by holding it in place for a short while once it has penetrated into the canal, to obtain an enlargement of the canal entrance, thus reducing the major interferences, in such a way as to afford an easy penetration of the instruments which follow.

In addition, the instrument according to the present invention has a rounded tip at the distal end, by means of which it is possible to avoid any risk of perforation of the pulp floor or of the canal walls.

Furthermore, the invention allows another major problem in dental treatment to be solved, namely the problem concerning the resumption of canal treatment. It does in fact happen that following an initial treatment of a canal, it is necessary to treat this canal once again for various reasons, for example a recurrence. It is thus necessary for the practitioner to extirpate from the canal the filling material or materials previously placed in the canal, which materials may be of various types.

In this case, the natural orifice of the canal is not available to the practitioner for introducing the instrument.

In a modified version of the instrument, it will be possible, by virtue of the upward movement of said instrument, to permit the formation of a pilot hole which will then allow the treatment to be continued in accordance with the normal methods.

Figure 5:
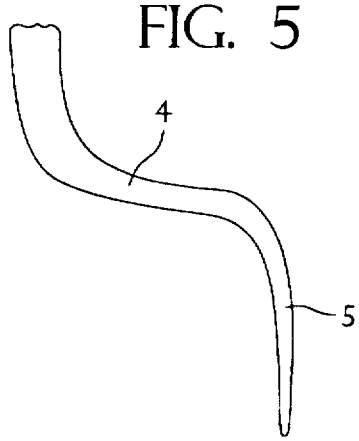
FIG. 5 represents an alternative embodiment of FIG. 4.
Figure 8:
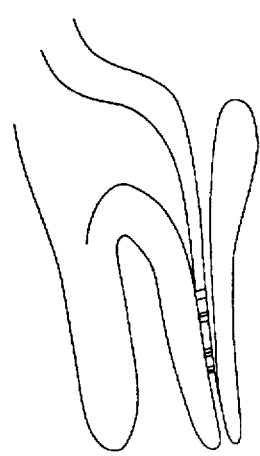
FIG. 8 shows, in cross section, the resumption of treatment on a tooth.

This version of the instrument, represented in FIG. 5, has a longer and finer distal portion (5) which is bent at approximately 90° in relation to the median portion (4). FIG. 8 shows the use of this alternative for the resumption of treatment in a tooth.

The invention can be applied to any type of handpiece, and this instrument can also be modified for retro treatment of the type described in the U.S. Pat. No. 5,320,530.

The principal advantages of the instrument according to the invention are in the main:

making it easier to reveal the canal entrance, suppressing the risks of incorrect routes which translate into perforations of the pulp floor or of the canal walls, permitting a flattening of the canal entrance, thus facilitating the penetration of the preparation instruments by suppression of the dentine stresses, improving the speed of treatment.

We claim:

1. A method for using an endodontic instrument comprising an elongated body having a proximal portion, a median portion, and a distal portion, wherein:

each of the proximal, median, and distal portions has a principal axis;

the proximal portion adjoins the median portion, and the median portion adjoins the distal portion;

the principal axis of the median portion forms a first angle with the principal axis of the proximal portion; and the principal axis of the distal portion forms a second angle with the principal axis of the median portion, wherein the first and second angles are in opposite directions, the method comprising the steps of:

(a) mounting the instrument onto a vibratory handpiece; and (b) using the instrument mounted onto the vibratory handpiece to widen an entrance of a tooth canal without perforating the pulp floor of the tooth canal, wherein the distal portion is prevented from reaching the pulp floor of the tooth canal by the median portion abutting the top of the outer wall of the tooth canal.

2. The method of claim 1, wherein the distal portion is further prevented from perforating the tooth canal walls.

3. The method of claim 2, wherein the end of the distal portion is rounded, and the cutting geometry of the distal portion is without helix and is a barb or a polygonal profile.

4. The method of claim 1, wherein the cutting geometry of the distal portion is without helix.

5. The method of claim 1, wherein the cutting geometry of the distal portion is a barb or a polygonal profile.

6. The method of claim 5, wherein the cutting geometry of the distal portion is without helix.

7. The method of claim 1, wherein the end of the distal portion is rounded.

8. The method of claim 1, wherein the distal portion does not go beyond the upper third of the root of a tooth.

* * * * *